(12) United States Patent
Ju et al.

(10) Patent No.: US 11,786,227 B2
(45) Date of Patent: Oct. 17, 2023

(54) TONGUE SEPARATION DEVICE

(71) Applicant: Samsung Life Public Welfare Foundation, Seoul (KR)

(72) Inventors: Sang Gyu Ju, Seoul (KR); Chae-Seon Hong, Gyeonggi-do (KR)

(73) Assignee: Samsung Life Public Welfare Foundation, Seoul (KR)

( * ) Notice: Subject to any disclaimer, the term of this patent is extended or adjusted under 35 U.S.C. 154(b) by 614 days.

(21) Appl. No.: 16/607,430

(22) PCT Filed: Mar. 28, 2018

(86) PCT No.: PCT/KR2018/003633
§ 371 (c)(1),
(2) Date: Oct. 23, 2019

(87) PCT Pub. No.: WO2018/199485
PCT Pub. Date: Nov. 1, 2018

(65) Prior Publication Data
US 2020/0146659 A1 May 14, 2020

(30) Foreign Application Priority Data
Apr. 26, 2017 (KR) .......................... 10-2017-0053853

(51) Int. Cl.
*A61B 13/00* (2006.01)
*A61B 6/10* (2006.01)

(52) U.S. Cl.
CPC .............. *A61B 13/00* (2013.01); *A61B 6/107* (2013.01)

(58) Field of Classification Search
CPC .. A61B 1/24; A61B 1/32; A61B 1/267; A61B 1/2673; A61B 1/2676;
(Continued)

(56) References Cited

U.S. PATENT DOCUMENTS 4,979,499 A * 12/1990 Sun ..................... A61B 1/267
600/187
5,533,523 A * 7/1996 Bass, Jr. ........... A61M 16/0497
128/859
(Continued)

FOREIGN PATENT DOCUMENTS

KR 10-2005-0051942 A 6/2005
KR 10-0938107 B1 1/2010
(Continued)

OTHER PUBLICATIONS

International Search Report and Written Opinion prepared by the Korean Intellectual Property Office, acting as the International Search Authority, for international application PCT/KR2018/003633 dated Jul. 2, 2018.

*Primary Examiner* — Jacqueline T Johanas
*Assistant Examiner* — Shannel Nicole Belk
(74) *Attorney, Agent, or Firm* — McCarter & English, LLP

(57) ABSTRACT

Provided is a tongue separation device including: a body unit including a contact surface fixing a tongue; a support unit arranged at one end portion of the body unit and supporting the body unit from outside a mouth; a tooth mounting unit arranged at one surface of the support unit adjacent to a first region of the body unit, mounting the teeth in a state where the body unit is inserted into the mouth, and including an upper surface mounting upper teeth among the teeth and a lower surface mounting lower teeth among the teeth; and a tongue position checking unit including an opening formed at the support unit to check a position of the tongue from outside the mouth.

17 Claims, 5 Drawing Sheets

(58) Field of Classification Search
CPC . A61B 1/00105; A61B 1/00154; A61B 13/00; A61B 6/107; A61C 5/90; A61C 5/82; A61F 5/56–566; A61M 16/0488; A61M 16/0493; A61M 16/0497; A61M 16/0495

See application file for complete search history.

(56) References Cited

U.S. PATENT DOCUMENTS

| | | | | |
|---|---|---|---|---|
| 5,590,643 | A * | 1/1997 | Flam | A61M 16/0488 128/207.14 |
| 6,378,522 | B1 * | 4/2002 | Pagan | A61M 16/0816 128/207.14 |
| 2005/0056282 | A1 * | 3/2005 | Robertson | A61M 16/0495 128/206.29 |
| 2005/0119526 | A1 | 6/2005 | Jeong et al. | |
| 2010/0030027 | A1 * | 2/2010 | Bastid | A61M 16/0488 600/120 |
| 2011/0126840 | A1 * | 6/2011 | Ogilvie | A61M 16/0488 128/207.14 |
| 2012/0143003 | A1 | 6/2012 | Anca et al. | |
| 2012/0283513 | A1 * | 11/2012 | Leeflang | A61B 1/00154 600/114 |
| 2013/0284181 | A1 * | 10/2013 | Guerra | A61M 16/0463 128/207.14 |
| 2017/0203067 | A1 * | 7/2017 | Eaton | A61M 16/0493 |

FOREIGN PATENT DOCUMENTS

| | | |
|---|---|---|
| KR | 20-2011-0004404 U | 5/2011 |
| KR | 10-1096881 B1 | 12/2011 |
| KR | 10-2016-0089974 A | 7/2016 |

* cited by examiner

TONGUE SEPARATION DEVICE

CROSS-REFERENCE TO RELATED APPLICATIONS

This application is the National Stage entry under 35 U.S.C. § 371 of International Application Number PCT/KR2018/003633 filed on Mar. 28, 2018, published on Nov. 1, 2018 under publication number WO 2018/199485 A1, which claims the benefit of priority under 35 U.S.C. § 119 of Korean patent application number 10-2017-0053853 filed Apr. 26, 2017.

TECHNICAL FIELD

Embodiments of the present disclosure relate to tongue separation devices.

BACKGROUND ART

Radiation therapy is a method of clinical medicine for treating patients by using radiation having very short wavelengths and high energy and is one of the three major cancer treatment methods, along with surgery and chemotherapy. Radiation therapy usually treats malignant tumors called cancers but also treats benign tumors and some benign diseases. Radiation therapy may be classified into external radiation therapy and brachytherapy according to the position of an irradiator.

External radiation therapy is a treatment method of irradiating radiation by using various pieces of equipment outside the body and may be classified into photon beam therapy, electron beam therapy, and particle beam therapy such as neutron therapy and proton therapy according to the type of radiation used. Meanwhile, brachytherapy is a method of irradiating radiation to a limited region by locating a radiation generator or radioactive isotopes in or on the body and may be classified into intracavitary therapy, intraluminal therapy, interstitial therapy, and contact therapy according to the insertion space or method thereof.

Meanwhile, when radiation therapy is performed, radiation may be irradiated only to a target region but radiation may actually be irradiated also to a region adjacent to a target region. Particularly, when radiation therapy is performed on a target region in the mouth, radiation may be irradiated also to the tongue or the oral mucosa, which is healthy tissue, to damage the tongue or the oral mucosa. Also, when radiation is irradiated farther than a planned beam path length due to a patient body shape variation or an uncertainty occurring in a treatment machine, it may cause damage to the tongue or peripheral normal organs due to unnecessary radiation irradiation thereto.

DESCRIPTION OF EMBODIMENTS

Technical Problem

In order to solve these problems, embodiments of the present disclosure provide tongue separation devices that may minimize damage to tongue tissues and oral mucosae during treatment by separating and fixing the tongue in one direction.

Solution to Problem

According to an aspect of the present disclosure, a tongue separation device includes: a body unit including a contact surface inserted into the mouth to fix the tongue in a state of pushing the tongue in one direction; a support unit arranged at one end portion of the body unit and supporting the body unit from outside the mouth; a tooth mounting unit arranged at one surface of the support unit adjacent to a first region of the body unit, mounting the teeth in a state where the body unit is inserted into the mouth, and including an upper surface mounting upper teeth among the teeth and a lower surface mounting lower teeth among the teeth; and a tongue position checking unit including an opening formed at the support unit to check a position of the tongue from outside the mouth, wherein a first portion of the contact surface of the body unit adjacent to the one end portion of the body unit is arranged over a virtual extension surface that passes through a center of the support unit and crosses between the upper surface and the lower surface of the tooth mounting unit, and a second portion of the contact surface of the body unit adjacent to the other end portion of the body unit is arranged under the virtual extension surface.

Advantageous Effects of Disclosure

The tongue separation device according to embodiments of the present disclosure may be inserted into the mouth to fix the tongue in a state of separating the tongue in one direction. This may ensure a safety distance from a treatment region to which radiation is irradiated during radiation therapy and thus may minimize radiation side effects. Particularly, the tongue separation device according to embodiments of the present disclosure may press the tongue from top to bottom to induce the tongue to be protruded forward as far as possible. This not only may minimize the radiation irradiation to the root of the tongue but also may effectively protect the tongue from the radiation irradiation in the case of treating both sides thereof because head-and-neck cancers are on both the left and right sides thereof.

BEST MODE

Figure 1:
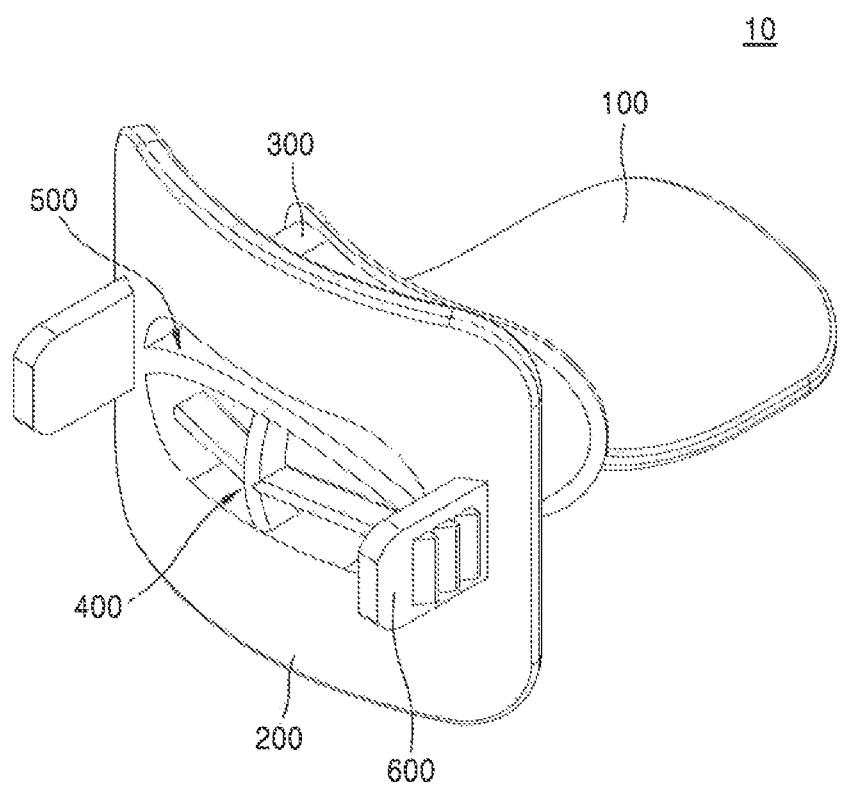
FIG. 1 is a perspective view illustrating a tongue separation device according to an embodiment of the present disclosure.

According to an aspect of the present disclosure, a tongue separation device includes: a body unit including a contact surface inserted into the mouth to fix the tongue in a state of pushing the tongue in one direction; a support unit arranged at one end portion of the body unit and supporting the body unit from outside the mouth; a tooth mounting unit arranged at one surface of the support unit adjacent to a first region of the body unit, mounting the teeth in a state where the body unit is inserted into the mouth, and including an upper surface mounting upper teeth among the teeth and a lower surface mounting lower teeth among the teeth; and a tongue position checking unit including an opening formed at the support unit to check a position of the tongue from outside the mouth, wherein a first portion of the contact surface of the body unit adjacent to the one end portion of the body unit is arranged over a virtual extension surface that passes through a center of the support unit and crosses between the upper surface and the lower surface of the tooth mounting unit, and a second portion of the contact surface of the body unit adjacent to the other end portion of the body unit is arranged under the virtual extension surface.

In an embodiment of the present disclosure, the tongue separation device may further include a coupling member capable of being coupled to an outer peripheral surface of the tooth mounting unit and including one or more bumps formed at an outer surface thereof to mount the teeth.

In an embodiment of the present disclosure, the coupling member may include a rubber or silicone material.

In an embodiment of the present disclosure, the tongue separation device may further include a first shielding member detachably attached to a second region of the body unit including the other end portion of the body unit, having a first thickness and a first length, and coupled to the body unit to increase at least one of a thickness and a length of the second region of the body unit.

In an embodiment of the present disclosure, the first shielding member may include an insertion groove formed to insert the second region of the body unit including the other end portion of the body unit.

In an embodiment of the present disclosure, the tongue separation device may further include a second shielding member detachably attached to the second region of the body unit, having a second thickness and a second length, and coupled to the body unit to increase at least one of the thickness and the length of the second region of the body unit, wherein the body unit may fix the tongue in a state where any one of the first shielding member and the second shielding member is coupled thereto.

In an embodiment of the present disclosure, the second thickness of the second shielding member may be different from the first thickness of the first shielding member.

In an embodiment of the present disclosure, the second length of the second shielding member may be different from the first length of the first shielding member.

In an embodiment of the present disclosure, the first shielding member and the second shielding member may include different materials.

In an embodiment of the present disclosure, the first shielding member and the second shielding member may include a same material.

In an embodiment of the present disclosure, the body unit may be formed to a uniform thickness.

In an embodiment of the present disclosure, a thickness of a second region of the body unit may be greater than a thickness of the first region of the body unit.

In an embodiment of the present disclosure, the tongue position checking unit may be formed at the support unit adjacent to the contact surface of the body unit.

In an embodiment of the present disclosure, the support unit may have a curved shape toward the body unit.

In an embodiment of the present disclosure, the tongue position checking unit may further include one or more supports partitioning the opening.

According to another aspect of the present disclosure, a tongue separation device includes: a body unit including a contact surface inserted into the mouth to fix the tongue in a state of pushing the tongue in a top-to-bottom direction; a support unit arranged at one end portion of the body unit and supporting the body unit from outside the mouth; and a first shielding member detachably attached to the body unit, having a first thickness and a first length, and coupled to the body unit to increase at least one of a thickness and a length of the body unit.

In an embodiment of the present disclosure, the tongue separation device may further include: a tooth mounting unit arranged at one surface of the support unit adjacent to a first region of the body unit, mounting the teeth in a state where the body unit is inserted into the mouth, and including an upper surface mounting upper teeth among the teeth and a lower surface mounting lower teeth among the teeth; and a tongue position checking unit including an opening formed at the support unit to check a position of the tongue from outside the mouth.

In an embodiment of the present disclosure, a first portion of the contact surface of the body unit adjacent to the one end portion of the body unit may be arranged over a virtual extension surface that passes through a center of the support unit and crosses between the upper surface and the lower surface of the tooth mounting unit, and a second portion of the contact surface of the body unit adjacent to the other end portion of the body unit may be arranged under the virtual extension surface.

Other aspects, features, and advantages other than those described above will become apparent from the accompanying drawings, the appended claims, and the detailed description of the disclosure.

Mode of Disclosure

The present disclosure may include various embodiments and modifications, and certain embodiments thereof are illustrated in the drawings and will be described herein in detail. The effects and features of the present disclosure and the accomplishing methods thereof will become apparent from the following description of the embodiments taken in conjunction with the accompanying drawings. However, the present disclosure is not limited to the embodiments described below but may be embodied in various modes.

Hereinafter, embodiments of the present disclosure will be described in detail with reference to the accompanying drawings, and in the following description, like reference numerals will denote like elements and redundant descriptions thereof will be omitted.

It will be understood that although terms such as "first" and "second" may be used herein to describe various components, these components should not be limited by these terms and these terms are only used to distinguish one component from another component.

As used herein, the singular forms "a", "an", and "the" are intended to include the plural forms as well, unless the context clearly indicates otherwise.

It will be understood that terms such as "comprise", "include", and "have" used herein specify the presence of stated features or components, but do not preclude the presence or addition of one or more other features or components.

It will be understood that when a layer, region, or component is referred to as being "on" another layer, region, or component, it may be "directly on" the other layer, region, or component or may be "indirectly on" the other layer, region, or component with one or more intervening layers, regions, or components therebetween.

Sizes of components in the drawings may be exaggerated for convenience of description. In other words, since the sizes and thicknesses of components in the drawings are arbitrarily illustrated for convenience of description, the present disclosure is not limited thereto.

When a certain embodiment may be implemented differently, a particular process order may be performed differently from the described order. For example, two consecutively described processes may be performed substantially at the same time or performed in an order opposite to the described order.

It will be understood that when a layer, region, or component is referred to as being "connected to" another layer, region, or component, it may be "directly connected to" the other layer, region, or component or may be "indirectly connected to" the other layer, region, or component with one or more intervening layers, regions, or components therebetween. For example, it will be understood that when a layer, region, or component is referred to as being "electrically connected to" another layer, region, or component, it may be "directly electrically connected to" the other layer, region, or component or may be "indirectly electrically connected to" the other layer, region, or component with one or more intervening layers, regions, or components therebetween.

Figure 2:
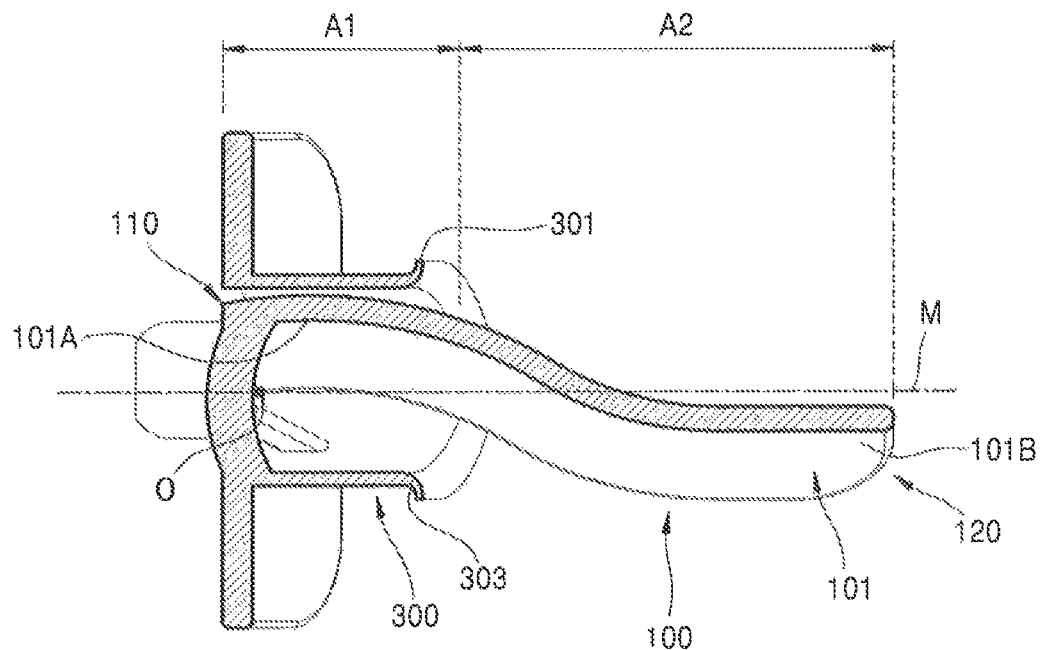
FIG. 2 is a cross-sectional view of the tongue separation device of FIG. 1.
Figure 3:
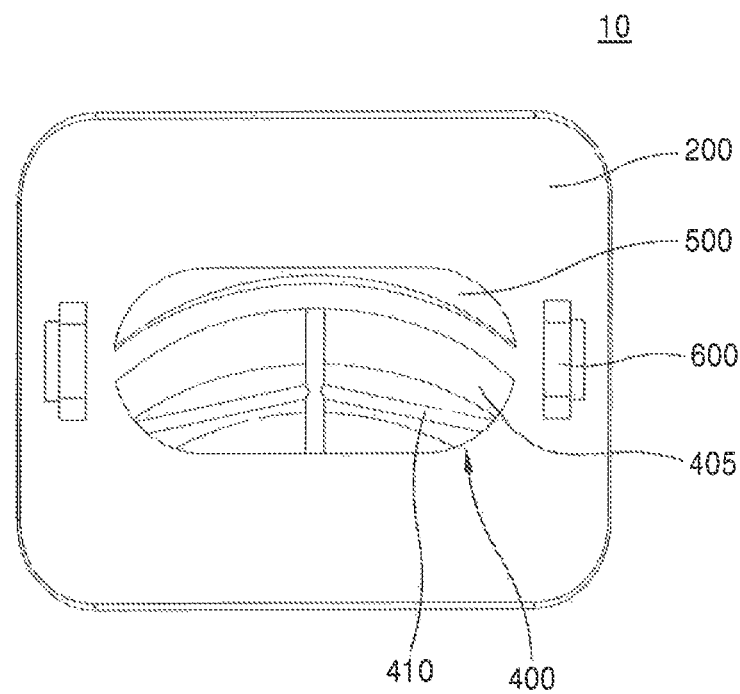
FIG. 3 is a front view of the tongue separation device of FIG. 1 viewed on the side of a support unit.

FIG. 1 is a perspective view illustrating a tongue separation device 10 according to an embodiment of the present disclosure, FIG. 2 is a cross-sectional view of the tongue separation device 10 of FIG. 1, and FIG. 3 is a front view of the tongue separation device 10 of FIG. 1 viewed on the side of a support unit 200.

Referring to FIGS. 1 to 3, the tongue separation device 10 according to an embodiment of the present disclosure may include a body unit 100, a support unit 200, a tooth mounting unit 300, a tongue position checking unit 400, and a ventilation unit 500. Also, the tongue separation device 10 may further include a fixing member 600.

The body unit 100 may include a contact surface 101 inserted into the mouth to fix the tongue in a state of pushing the tongue in one direction. The contact surface 101 may have a concave shape in the lengthwise direction of the body unit 100 to cover the tongue. A detailed shape of the body unit 100 will be described below.

The support unit 200 may be arranged at one end portion 110 of the body unit 100 and may support the body unit 100 from outside the mouth. The support unit 200 may have a curved shape toward the body unit 100. In this case, not all the support unit 200 has to be curved. Because one surface of the support unit 200 adjacent to the body unit 100 directly contacts the lips of a user, at least one surface of the support unit 200 may have a curved shape toward the body unit 100. The curvature of one surface of the support unit 200 may vary according to users.

Meanwhile, the support unit 200 may have a width larger than the width of the body unit 100 in the widthwise direction of the body unit 100. Accordingly, the support unit 200 may support the body unit 100 from outside the mouth such that the body unit 100 may not be inserted into the mouth to more than a certain depth.

The tooth mounting unit 300 may be arranged at one surface of the support unit 200 adjacent to a first region A1 of the body unit 100 and may mount the teeth in a state where the body unit 100 is inserted into the mouth. In this case, the tooth mounting unit 300 may include an upper surface 301 for mounting upper teeth among the teeth and a lower surface 303 for mounting lower teeth among the teeth. The tooth mounting unit 300 may be formed to cover the first region A1 of the body unit 100 adjacent to the support unit 200. Although not illustrated, the tooth mounting unit 300 may include a plurality of protrusions formed in a direction perpendicular to the lengthwise direction of the body unit 100. In another embodiment, the tooth mounting unit 300 may be formed to include a plurality of grooves formed in a direction perpendicular to the lengthwise direction of the body unit 100. The tooth mounting unit 300 may be arranged at a position where the teeth are naturally located when the mouth is closed in a state where the body unit 100 is inserted into the mouth, and may be formed to include bumps to stably fix the body unit 100 when the user's teeth are caught by the bumps.

The tongue position checking unit 400 may include an opening 405 passing through the support unit 200 in order to be able to check the position of the tongue from outside the mouth. The tongue position checking unit 400 may be formed in one region of the support unit 200 adjacent to the contact surface 101 of the body unit 100. The tongue separation device 10 may allow an inspector to check whether the tongue of the user who is a patient is properly separated, even from the outside through the tongue position checking unit 400 during the radiation therapy.

Also, the tongue position checking unit 400 may include one or more supports 410 partitioning the opening 405. Although a case of including a cross-shaped support 410 is illustrated in the drawings, the present disclosure is not limited thereto and a straight support may be used. The user not only may grasp a designated position of the tongue by touching the tongue to the support 410 but also may simultaneously prevent the tongue from passing through the opening 405. Although not illustrated, in another embodiment, the tongue position checking unit 400 may further include a protrusion portion (not illustrated) protruding in the extension direction of the body unit 100 with respect to one surface of the support unit 200 contacting the body unit 100. The protrusion portion (not illustrated) may be located at the center of the opening 405 by using the support 410 described above. The protrusion portion (not illustrated) may stimulate a tip portion of the user's tongue to inform the user that the tongue is properly located. Accordingly, the tongue position checking unit 400 may check the position of the tongue from the outside through the opening 405 and simultaneously allow the user to grasp a designated position of the tongue, thus ensuring the position reproducibility of the tongue. In the case of including the protrusion portion (not illustrated), the protrusion length of the protrusion portion (not illustrated) may be determined corresponding to the length of the user's tongue. Also, the protrusion portion (not illustrated) may induce the patient to pull out the tongue by inducing the patient to touch the tip of the tongue to the protrusion portion, and in this case, the radiation to the root of the tongue may be reduced as the patient's tongue is separated outside the mouth.

Meanwhile, the tongue separation device 10 may further include the ventilation unit 500 and the fixing member 600.

The ventilation unit 500 may be formed in one region of the support unit 200 so as to communicate from the separation space between the body unit 100 and the upper surface 301 of the tooth mounting unit 300 to the outside of the support unit 200. Particularly, the ventilation unit 500 may be formed at the support unit 200 at a position opposite to the tongue position checking unit 400 with respect to the body unit 100. In this case, the ventilation unit 500 may be a hole for connecting the separation space in the mouth to the outside of the mouth in a state where the user's tongue is separated and may induce the user to breathe comfortably even with the tongue separation device 10 in the mouth. Also, because the ventilation unit 500 is formed horizontally with respect to the upper surface 301 and the lower surface 303 of the tooth mounting unit 300, the user may breathe horizontally uniformly in the mouth.

The fixing member 600 may be located at the other surface of the support unit 200 facing the body unit 100 and may fix the tongue separation device 10 to an external device (not illustrated) such as a mask device. The tongue separation device 10 may include one or more fixing members 600 and may include two fixing members 600 protruding from the support unit 200, as illustrated in the drawings. When two fixing members 600 are included, protrusions having an inclination may be formed at the outer surfaces of the fixing members 600 that do not face each other. The fixing member 600 may also function as a handle for holding the tongue separation device 10. However, the present disclosure is not limited in the shape of the fixing member 600, and it may be coupled with an external device (not illustrated) through a plurality of grooves (not illustrated) formed to pass through the support unit 200.

Hereinafter, a detailed description will be given of the body unit 100 of the tongue separation device 10 according to an embodiment of the present disclosure.

The body unit 100 may include a first region A1 adjacent to the support unit 200 and a second region A2 for directly pressing the tongue. The body unit 100 may be arranged horizontally with respect to a virtual extension surface M that passes through a center O of the support unit 200 and crosses between the upper surface 301 and the lower surface 303 of the tooth mounting unit 300. In other words, the widthwise direction of the body unit 100 may be parallel to the virtual extension surface M. By the body unit 100, the tongue separation device 10 may fix the user's tongue while pressing the user's tongue in the top-to-bottom direction. In this case, a first portion 101A of the contact surface 101 of the body unit 100 adjacent to one end portion 110 of the body unit 100 may be arranged over the virtual extension surface M. Also, a second portion 101B of the contact surface 101 of the body unit 100 adjacent to the other end portion 120 of the body unit 100 may be arranged under the virtual extension surface M.

Particularly, because the second portion 101B separated from the support unit 200 is arranged lower than the first portion 101A adjacent to the support unit 200, the body unit 100 may fix the tongue while pressing the tongue from top to bottom. Particularly, the body unit 100 may press down a root portion of the tongue by the second portion 101B to guide and protrude the tongue forward as far as possible, thereby minimizing the radiation to the root of the tongue.

Because the first portion 101A and the second portion 101B of the contact surface 101 of the body unit 100 are arranged at opposite positions with respect to the virtual extension surface M, the body unit 100 may include a connection surface connecting the first portion 101A to the second portion 101B and the connection surface may meet the virtual extension surface M. The connection surface may have different curvature directions with respect to the virtual extension surface M; for example, the connection surface adjacent to the support unit 200 may be concave downward and the connection surface relatively separated from the support unit 200 may be concave upward. The contact surface 101 of the body unit 100 of the tongue separation device 10 may be formed as a streamlined curved surface, thereby minimizing inconvenience when the user wears the tongue separation device 10 in the mouth. However, the present disclosure is not limited thereto, and the body unit 100 may be manufactured in various shapes corresponding to the mouth structures of users.

In an embodiment, the body unit 100 may have a uniform thickness in the lengthwise direction thereof. In other words, the body unit 100 may have a uniform thickness in the first region A1 and the second region A2. However, the present disclosure is not limited thereto. In another embodiment, the thickness of the body unit 100 in the second region A2 may be greater than the thickness of the body unit 100 in the first region A1. The second region A2 of the body unit 100 may be a region directly contacting the tongue and also a region for shielding radiation. Thus, the second region A2 of the body unit 100 may be formed thicker than the first region A1. The thickness of the second region A2 may be designed to be patient-customized to correspond to the mouth structure of the patient and the mouth opening/closing function before/after surgery. The length of the second region A2 of the body unit 100 may also be designed to be patient-customized.

In an embodiment, the tongue separation device 10 may be manufactured by a three-dimensional (3D) printer. The tongue separation device 10 should be designed in various forms according to the mouth structures of users. Manufacturing the tongue separation device 10 in various structures and forms by injection molding may be costly and time-consuming. Thus, by manufacturing the tongue separation device 10 by a 3D printer by storing standard data, measuring the mouth structures of users, and then making modifications by the difference from the standard data, it may be possible to provide rapid treatment and reduce the manufacturing cost.

In addition, the tongue separation device 10 may be formed of a hard material. The tongue separation device 10 may be formed of a material with a certain hardness to accurately push the tongue in one direction during radiation therapy. In another embodiment, the interior of the body unit 100 of the tongue separation device 10 may be formed of a hard material and the surface thereof may be formed of a flexible material. Because the body unit 100, particularly the second region A2, of the tongue separation device 10 directly contacts the user's body, it may cause inconvenience to the user according to the material thereof and therefore the surface thereof may be formed of a flexible material to minimize the inconvenience. For example, the interior of the tongue separation device 10 may include a material with a certain hardness, such as plastic, metal, or ceramic, and the surface of the tongue separation device 10 may include a flexible material such as silicone, rubber, fluorine resin (known as Teflon resin) (such as polytetrafluoroethylene (PTEE), hexafluoropropylene copolymer (FEP), or perfluoro alkylvinylether copolymer (PFA)), polyethylene, polystyrene, polyester, polyimide, polyamide, or polyurethane. The tongue separation device 10 may function as a radiation shield to prevent unnecessary radiation interference to the tongue or peripheral normal organs when planned radiation beams such as proton beams are increased by various uncertainties, such as radiation being irradiated past the tumor.

Figure 4:
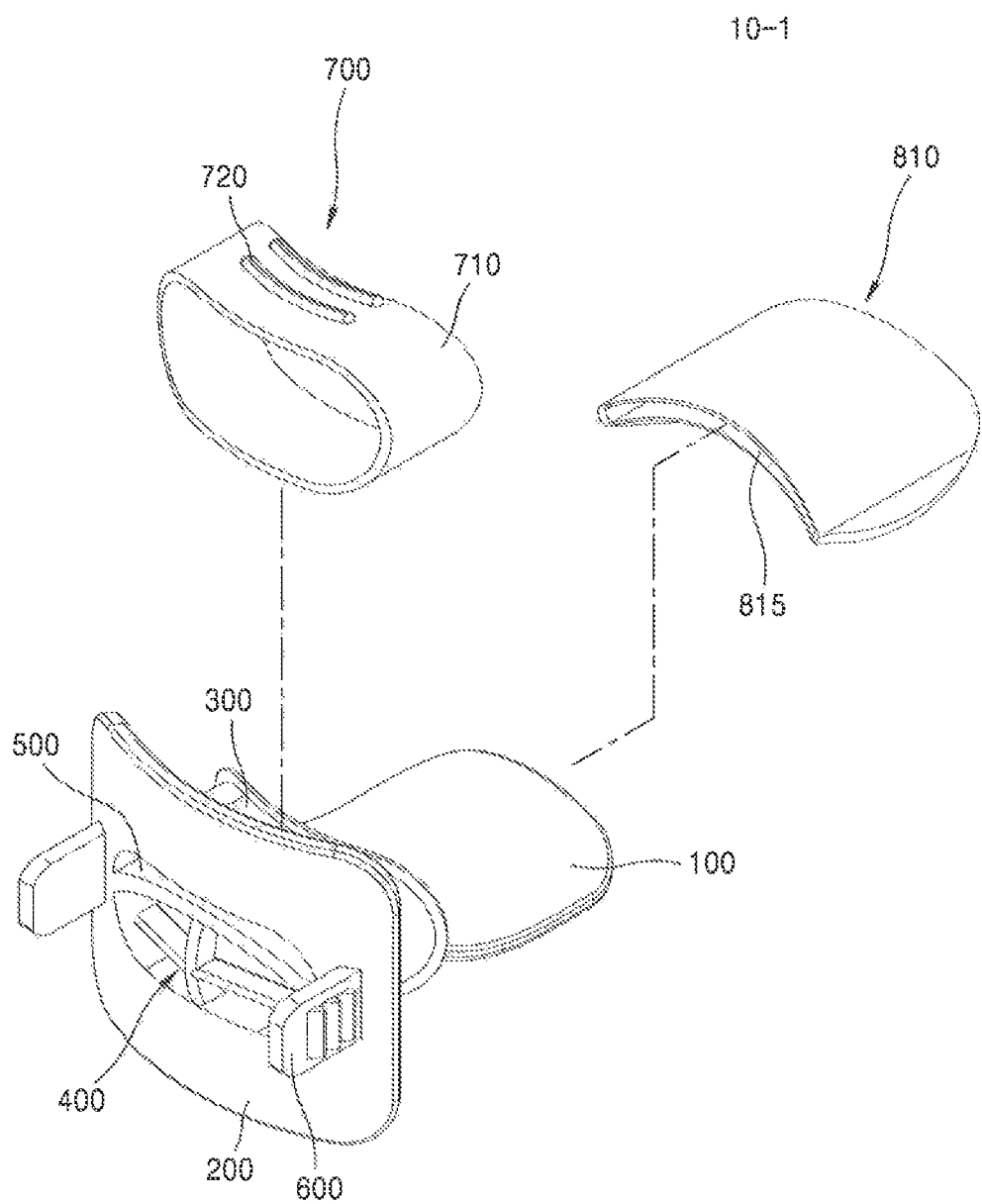
FIG. 4 is an exploded perspective view schematically illustrating a tongue separation device according to another embodiment of the present disclosure.
Figure 5:
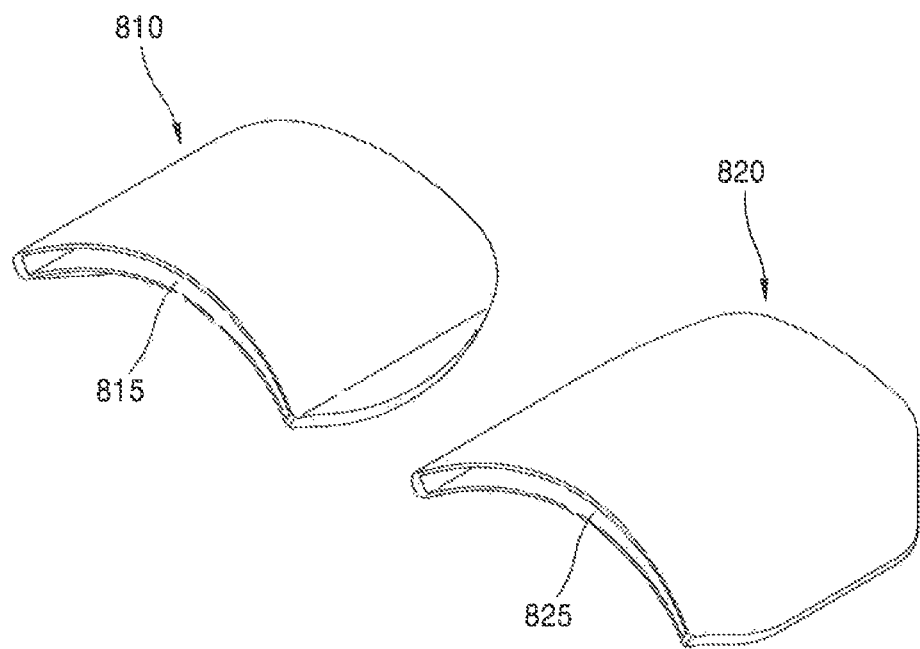
FIG. 5 is a perspective view illustrating a first shielding member and a second shielding member of FIG. 4.

FIG. 4 is an exploded perspective view schematically illustrating a tongue separation device 10-1 according to another embodiment of the present disclosure, FIG. 5 is a perspective view illustrating a first shielding member 810 and a second shielding member 820 of FIG. 4, and FIGS. 6A to 6C are diagrams illustrating example modes of applying the first shielding member 810 or the second shielding member 820 to the tongue separation device 10-1 of FIG. 4.

Referring to FIG. 4, the tongue separation device 10-1 according to another embodiment of the present disclosure may include a body unit 100, a support unit 200, a tooth mounting unit 300, a tongue position checking unit 400, a ventilation unit 500, a coupling member 700, a first shielding member 810, and a second shielding member 820. The components other than the coupling member 700, the first shielding member 810, and the second shielding member 820 in the tongue separation device 10-1 according to another embodiment are the same as those described above, and thus redundant descriptions thereof will be omitted for conciseness.

The body unit 100 may include a contact surface 101 inserted into the mouth to fix the tongue in a state of pushing the tongue in one direction. The support unit 200 may be arranged at one end portion 110 of the body unit 100 and may support the body unit 100 from outside the mouth. The tooth mounting unit 300 may be arranged at one surface of the support unit 200 adjacent to a first region A1 of the body unit 100 and may mount the teeth in a state where the body unit 100 is inserted into the mouth. The tongue position checking unit 400 may include an opening 405 passing through the support unit 200 in order to be able to check the position of the tongue from outside the mouth. The ventilation unit 500 may be formed in one region of the support unit 200 so as to communicate from the separation space between the body unit 100 and the upper surface 301 of the tooth mounting unit 300 to the outside of the support unit 200.

The coupling member 700 may be coupled to the outer peripheral surface of the tooth mounting unit 300 and one or more bumps 720 may be formed at an outer surface 710 of the coupling member 700 to mount the teeth. The coupling member 700 may be inserted into the mouth in a state of being mounted on the tooth mounting unit 300 and may be arranged at a position where the teeth are naturally located when the user closes the mouth. In this case, the coupling member 700 may be formed to include one or more bumps 720 to stably fix the body unit 100 when the user's teeth are caught by the bumps 720. In another embodiment, the coupling member 700 may include, instead of the bumps 720, a plurality of protrusions formed in a direction perpendicular to the lengthwise direction of the body unit 100. Meanwhile, the coupling member 700 may perform a function for more stably mounting the user's teeth and may be formed of a material different from that of the tooth mounting unit 300. For example, the coupling member 700 may be formed of a flexible material such as silicone, rubber, fluorine resin (known as Teflon resin) (such as polytetrafluoroethylene (PTEE), hexafluoropropylene copolymer (FEP), or perfluoro alkylvinylether copolymer (PFA)), polyethylene, polystyrene, polyester, polyimide, polyamide, or polyurethane.

The coupling member 700 may increase the thickness of the tooth mounting unit 300 by being mounted on the tooth mounting unit 300. The tongue separation device 10 may include one or more coupling members 700, and in this case, the coupling members 700 may have different thicknesses and thus may be interchangeably mounted according to the user's mouth structure. Also, as illustrated, the coupling member 700 may be in the form of a ring and may be fitted in the direction of the other end portion of the body unit 100. However, the present disclosure is not limited thereto, and in another embodiment, the coupling member 700 may be formed in a C shape and mounted through the side of the tooth mounting unit 300.

Referring to FIGS. 4 and 5, the first shielding member 810 may be detachably attached to the second region A2 of the body unit 100 including the other end portion 120 of the body unit 100 and may be coupled to the body unit 100 to increase at least one of the thickness and the length of the second region A2 of the body unit 100. The first shielding member 810 may have a first thickness and a first length and may be mounted on the body unit 100 to increase the thickness or the length of the body unit 100 by the first thickness or the first length. The first shielding member 810 may be formed to include an insertion groove 815 into which the second region A2 of the body unit 100 may be inserted. The first shielding member 810 may be mounted on the second region A2 of the body unit 100 by inserting the other end portion 120 of the body unit 100 into the insertion groove 815.

Like the first shielding member 810, the second shielding member 820 may be detachably attached to the second region A2 of the body unit 100 including the other end portion 120 of the body unit 100 and may be coupled to the body unit 100 to increase at least one of the thickness and the length of the second region A2 of the body unit 100. The second shielding member 820 may have a second thickness and a second length and may be mounted on the body unit 100 to increase the thickness or the length of the body unit 100 by the second thickness or the second length.

Figure 6A:
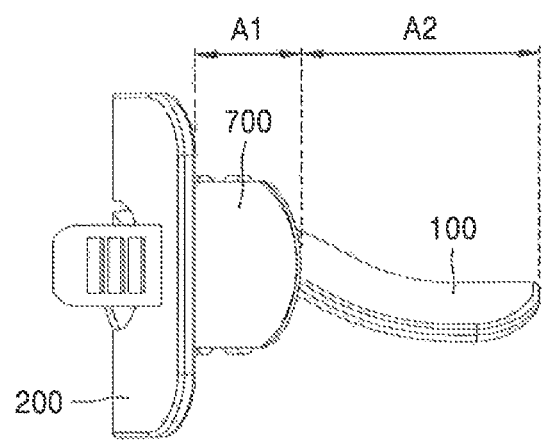
FIGS. 6A to 6C are diagrams illustrating example modes of applying the first shielding member or the second shielding member to the tongue separation device of FIG. 4.
Figure 6B:
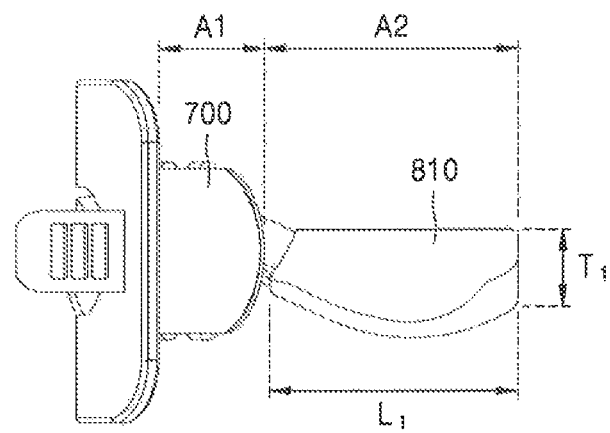
Figure 6C:
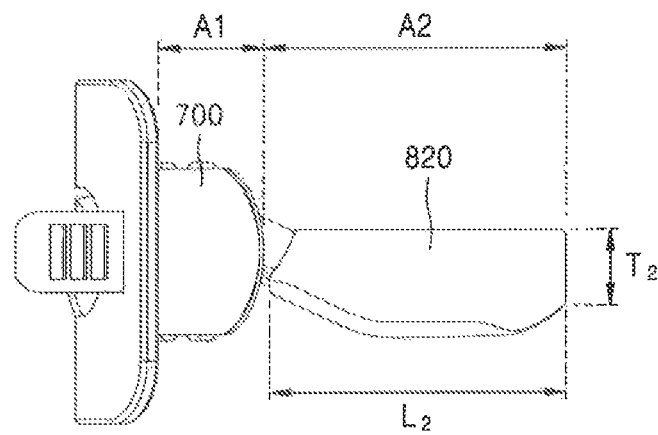

Referring to FIGS. 6A to 6C, any one of the first shielding member 810 and the second shielding member 820 may be coupled to the body unit 100 as necessary. The tongue separation device 10-1 may be used without the first shielding member 810 or the second shielding member 820 as illustrated in FIG. 6A. Alternatively, the tongue separation device 10-1 may be used with the first shielding member 810 mounted thereon as illustrated in FIG. 6B or may be used with the second shielding member 820 mounted thereon as illustrated in FIG. 6C.

In this case, the thickness or length of the body unit 100 may vary according to the thickness or length of the selected first shielding member 810 or the second shielding member 820. In other words, a first thickness T1 of the first shielding member 810 may be different from a second thickness T2 of the second shielding member 820, and a first length L1 thereof may be different from a second length L2 thereof. Thus, in the tongue separation device 10-1, any one of the first shielding member 810 and the second shielding member 820 may be selected and mounted on the body unit 100 according to the user's mouth structure. Although the case of including the first shielding member 810 and the second shielding member 820 has been mainly described above, this is merely an embodiment and the present disclosure is not limited thereto. In another embodiment, the tongue separation device 10 may include a plurality of shielding members having different thicknesses and lengths and may be used in a state where the plurality of shielding members are selectively mounted on the body unit 100 according to users.

Meanwhile, the first shielding member 810 and the second shielding member 820 may include the same material. For example, the first shielding member 810 and the second shielding member 820 may be formed of a flexible material such as silicone, rubber, fluorine resin (known as Teflon resin) (such as polytetrafluoroethylene (PTEE), hexafluoropropylene copolymer (FEP), or perfluoro alkylvinylether copolymer (PFA)), polyethylene, polystyrene, polyester, polyimide, polyamide, or polyurethane. In another embodiment, the first shielding member 810 and the second shielding member 820 may include different materials. Any one of the first shielding member 810 and the second shielding member 820 may include a flexible material selected from the above materials and the other one may include a hard material.

As described above, the tongue separation device according to embodiments of the present disclosure may be inserted into the mouth to fix the tongue in a state of separating the tongue in one direction. This may ensure a safety distance from a treatment region to which radiation is irradiated during radiation therapy and thus may minimize radiation side effects. Particularly, the tongue separation device according to embodiments of the present disclosure may press the tongue from top to bottom to induce the tongue to be protruded forward as far as possible. This not only may minimize the radiation irradiation to the root of the tongue but also may effectively protect the tongue from the radiation irradiation in the case of treating both sides thereof because head-and-neck cancers are on both the left and right sides thereof.

Although the present disclosure has been described with reference to the embodiments illustrated in the drawings, this is merely an example and those of ordinary skill in the art will understand that various modifications may be made therein. Thus, the spirit and scope of the present disclosure should be defined by the technical spirit of the appended claims.

INDUSTRIAL APPLICABILITY

According to the present disclosure, a tongue separation device is provided. Also, embodiments of the present disclosure may be applied to radiation therapy or the like used in the industry.

The invention claimed is:

1. A tongue separation device comprising:
a body unit including a contact surface configured to be inserted into a mouth to fix a tongue in a state of pushing the tongue in one direction;
a support unit arranged at one end portion of the body unit and supporting the body unit from outside the mouth;
a tooth mounting unit arranged at one surface of the support unit adjacent to a first region of the body unit, configured to mount the teeth in a state where the body unit is inserted into the mouth, and including an upper surface configured to mount upper teeth among the teeth and a lower surface configured to mount lower teeth among the teeth; and
a tongue position checking unit including an opening formed at the support unit to check a position of the tongue from outside the mouth,
wherein a first portion of the contact surface of the body unit adjacent to the one end portion of the body unit is arranged over a virtual extension surface that passes through a center of the support unit and crosses between the upper surface and the lower surface of the tooth mounting unit,
a second portion of the contact surface of the body unit adjacent to another end portion of the body unit is arranged under the virtual extension surface, and
the tongue position checking unit includes one or more supports extending between inner surfaces of the opening and disposed across the opening, wherein the one or more supports are in a cross shape and each end of the one or more supports is curved inward towards the body unit, and
a pair of fixing members protruding from an opposite side of one side of the support unit facing the body unit, wherein the pair of fixing members are provided with protrusions having an inclination on surfaces that do not face each other.

2. The tongue separation device of claim 1, further comprising
a coupling member capable of being coupled to an outer peripheral surface of the tooth mounting unit and including one or more bumps formed at an outer surface thereof to mount the teeth.

3. The tongue separation device of claim 2, wherein the coupling member comprises a rubber or silicone material.

4. The tongue separation device of claim 1, further comprising
a first shielding member detachably attached to a second region of the body unit including the other end portion of the body unit, having a first thickness and a first length, and coupled to the body unit to increase at least one of a thickness and a length of the second region of the body unit, and
wherein the one end portion of the body unit is disposed on the first region and the other end portion of the body unit is disposed on the second region.

5. The tongue separation device of claim 4, wherein the first shielding member includes an insertion groove formed to insert the second region of the body unit including the other end portion of the body unit.

6. The tongue separation device of claim 4, further comprising
a second shielding member detachably attached to the second region of the body unit, having a second thickness and a second length, and coupled to the body unit to increase at least one of the thickness and the length of the second region of the body unit,
wherein the body unit fixes the tongue in a state where the body unit is coupled to the first shielding member or the second shielding member.

7. The tongue separation device of claim 6, wherein the second thickness of the second shielding member is different from the first thickness of the first shielding member.

8. The tongue separation device of claim 6, wherein the second length of the second shielding member is different from the first length of the first shielding member.

9. The tongue separation device of claim 6, wherein the first shielding member and the second shielding member comprise different materials.

10. The tongue separation device of claim 6, wherein the first shielding member and the second shielding member comprise a same material.

11. The tongue separation device of claim 1, wherein the body unit is formed to a uniform thickness.

12. The tongue separation device of claim 1, wherein a thickness of a second region of the body unit is greater than a thickness of the first region of the body unit.

13. The tongue separation device of claim 1, wherein the tongue position checking unit is disposed at the support unit adjacent to the contact surface of the body unit.

14. The tongue separation device of claim 1, wherein the support unit has a curved shape toward the body unit.

15. A tongue separation device comprising:
a body unit including a contact surface configured to be inserted into a mouth to fix a tongue in a state of pushing the tongue in a top-to-bottom direction;
a support unit arranged at one end portion of the body unit and supporting the body unit from outside the mouth;
a first shielding member detachably attached to the body unit, having a first thickness and a first length, and coupled to the body unit to increase at least one of a thickness and a length of the body unit, and a tongue position checking unit including an opening formed at the support unit and one or more supports extending between inner surfaces of the opening and disposed across the opening, wherein the one or more supports are in a cross shape and each end of the one or more supports is curved inward towards the body unit, and a pair of fixing members protruding from an opposite side of one side of the support unit facing the body unit, wherein the pair of fixing members are provided with protrusions having an inclination on surfaces that do not face each other.

16. The tongue separation device of claim 15, further comprising:

a tooth mounting unit arranged at one surface of the support unit adjacent to a first region of the body unit, mounting the teeth in a state where the body unit is inserted into the mouth, and including an upper surface mounting upper teeth among the teeth and a lower surface mounting lower teeth among the teeth; and wherein the tongue position checking unit is configured to check a position of the tongue from outside the mouth.

17. The tongue separation device of claim 16, wherein a first portion of the contact surface of the body unit adjacent to the one end portion of the body unit is arranged over a virtual extension surface that passes through a center of the support unit and crosses between the upper surface and the lower surface of the tooth mounting unit, and a second portion of the contact surface of the body unit adjacent to the other end portion of the body unit is arranged under the virtual extension surface.

* * * * *